(12) United States Patent
Madden et al.

(10) Patent No.: US 10,744,180 B2
(45) Date of Patent: *Aug. 18, 2020

(54) THERAPY AND KIT FOR THE PREVENTION AND TREATMENT OF CYSTIC FIBROSIS

(71) Applicant: Trustees of Dartmouth College, Hanover, NH (US)

(72) Inventors: Dean R. Madden, Hanover, NH (US); Nicholas P. Gill, White River Junction, VT (US); Carrie Ann Davison, Florence, AL (US); Mark R. Spaller, White River Junction, VT (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 10 days.

This patent is subject to a terminal disclaimer.

(21) Appl. No.: 15/820,962

(22) Filed: Nov. 22, 2017

(65) Prior Publication Data
US 2018/0318382 A1  Nov. 8, 2018

Related U.S. Application Data

(63) Continuation-in-part of application No. PCT/US2016/033476, filed on May 20, 2016, which is a continuation of application No. 14/719,910, filed on May 22, 2015, now Pat. No. 9,421,239.

(60) Provisional application No. 62/506,952, filed on May 16, 2017.

(51) Int. Cl.
| | |
|---|---|
| A61K 38/00 | (2006.01) |
| C07K 14/47 | (2006.01) |
| A61K 38/08 | (2019.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 45/06 | (2006.01) |
| A61K 31/655 | (2006.01) |
| A61K 31/15 | (2006.01) |
| A61K 38/10 | (2006.01) |
| A61K 38/16 | (2006.01) |
| C07K 5/103 | (2006.01) |
| C07K 7/06 | (2006.01) |
| C07K 7/08 | (2006.01) |

(52) U.S. Cl.
CPC ............ *A61K 38/08* (2013.01); *A61K 31/15* (2013.01); *A61K 31/655* (2013.01); *A61K 38/04* (2013.01); *A61K 38/10* (2013.01); *A61K 38/16* (2013.01); *A61K 45/06* (2013.01); *C07K 5/1013* (2013.01); *C07K 7/06* (2013.01); *C07K 7/08* (2013.01); *C07K 14/4703* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 8,278,278 | B2 | 10/2012 | Malkas et al. | 514/19.3 |
| 8,415,292 | B2 * | 4/2013 | Madden | A61K 38/08 |
| | | | | 514/1.8 |
| 8,999,919 | B2 * | 4/2015 | Madden | A61K 38/00 |
| | | | | 435/375 |
| 9,333,235 | B2 * | 5/2016 | Madden | C07K 7/06 |
| 9,421,239 | B2 * | 8/2016 | Madden | A61K 31/655 |
| 2005/0196754 | A1 | 9/2005 | Drmanac et al. | 435/6.11 |
| 2005/0214791 | A1 | 9/2005 | Sheppard et al. | 435/6.14 |
| 2005/0282743 | A1 | 12/2005 | Lu et al. | 514/1.2 |
| 2007/0044171 | A1 | 2/2007 | Kovalic et al. | 800/278 |
| 2007/0061916 | A1 | 3/2007 | Kovalic et al. | 800/278 |
| 2008/0069838 | A1 | 3/2008 | Peiris et al. | 424/221.1 |
| 2011/0201544 | A1 * | 8/2011 | Madden | A61K 38/08 |
| | | | | 514/1.8 |
| 2012/0071396 | A1 * | 3/2012 | Madden | A61K 38/00 |
| | | | | 514/1.8 |
| 2014/0100155 | A1 * | 4/2014 | Madden | C07K 7/06 |
| | | | | 514/1.8 |
| 2014/0296164 | A1 * | 10/2014 | Mallon | C07K 7/06 |
| | | | | 514/21.6 |

FOREIGN PATENT DOCUMENTS

| | | | | |
|---|---|---|---|---|
| WO | WO 03/004604 A2 | 1/2003 | | |
| WO | WO-2010048125 A2 * | 4/2010 | ............ | A61K 38/08 |
| WO | WO-2013070529 A1 * | 5/2013 | ............ | A61K 38/00 |
| WO | WO-2013070531 A1 * | 5/2013 | ............ | A61K 38/00 |

OTHER PUBLICATIONS

Anonymous "About Cystic Fibrosis" https://www.cff.org/What-is-CF/About-Cystic-Fibrosis/ Cystic Fibrosis Foundation. (Year: 2019).*
Anonymous "Cystic Fibrosis: Preventing Cystic Fibrosis" https://www.blf.org.uk/support-for-you/cystic-fibrosis/prevention British Lung Foundation. (Year: 2019).*
Anonymous "Cystic Fibrosis Overview" https://www.mayoclinic.org/diseases-conditions/cystic-fibrosis/symptoms-causes/syc-20353700 Mayo Clinic. (Year: 2016).*
Amacher et al. "Crystallization and Preliminary Diffraction Analysis of the CAL PDZ Domain in Complex with a Selective Peptide Inhibitor" Acta Crystallographica 2011 F67:600-603.
Bossard et al. "NHE-RF1 Protein Rescues ΔF508-CFTR Function" American Journal of Physiology—Lung Cellular and Molecular Physiology 2007 292: L1085-L1094.

(Continued)

*Primary Examiner* — James H Alstrum-Acevedo
*Assistant Examiner* — Zachary J Miknis
(74) *Attorney, Agent, or Firm* — Licata & Tyrrell P.C.

(57) ABSTRACT

Compositions, kits and methods for preventing or treating cystic fibrosis are provided, which include the use of a peptidomimetic that inhibits the interaction between CAL and mutant CFTR proteins.

8 Claims, No Drawings
Specification includes a Sequence Listing.

(56) References Cited

OTHER PUBLICATIONS

Chen et al. "Computational Structure-based Redesign of Enzyme Activity" Proceedings of the National Academy of Sciences USA 2009 106(10):3764-3769.

Cheng et al. "A Golgi-associated PDZ Domain Protein Modulates Cystic Fibrosis Transmembrane Regulator Plasma Membrane Expression" The Journal of Biological Chemistry 2002 277(5):3520-3529.

Cheng et al. "Defective Intracellular Transport and Processing of CFTR is the Molecular Basis of Most Cystic Fibrosis" Cell 1990 63:827-834.

Cushing et al. "The Relative Binding Affinities of PDZ Partners for CFTR: a Biochemical Basis for Efficient Endocytic Recycling" Biochemistry 2008 47:10084-10098.

Dalemans et al. "Altered Chloride Ion Channel Kinetics Associated with the ΔF508 Cystic Fibrosis Mutation" Nature 1991 354:526-528.

Dasenbrook et al. "Persistent Methicillin-Resistant *Staphylococcus aureus* and Rate of $FEV_1$ Decline in Cystic Fibrosis" American Journal of Respiratory and Critical Care Medicine 2008 178:814-821.

Denning et al. "Processing of Mutant Cystic Fibrosis Transmembrane Conductance Regulator Is Temperature-Sensitive" Nature 1992 358:761-764.

Drumm et al. "Chloride Conductance Expressed by ΔF508 and Other Mutant CFTRs in *Xenopus oocytes*" Science 1991 254:1797-1799.

Flume et al. "Ivacaftor in Subjects with Cystic Fibrosis Who Are Homozygous for the F508del-CFTR Mutation" Chest 2012 142(3):718-724.

Frey et al. "Predicting Resistant Mutations Using Protein Design Algorithms" Proceedings of the National Academy of Sciences USA 2010 107(31):13707-13712.

Georgiev et al. "The Minimized Dead-end Elimination Criterion and its Application to Protein Redesign in a Hybrid Scoring and Search Algorithm for Computing Partition Functions over Molecular Ensembles" Journal of Computational Chemistry 2008 29(10):1527-1542.

Guerra et al. "$Na^+/H^+$• Exchanger Regulatory Factor Isoform 1 Overexpression Modulates Cystic Fibrosis Transmembrane Conductance Regulator (CFTR) Expression and Activity in Human Airway 16HBE14o-Cells and Rescues ΔF508 CFTR Functional Expression in Cystic Fibrosis Cells" The Journal of Biological Chemistry 2005 280(49):40925-40933.

Guggino, W.B. and Stanton, B.A. "New Insights into Cystic Fibrosis: Molecular Switches that Regulate CFTR" Nature Reviews Molecular Cell Biology 2006 7(6):426-436.

Kerem et al. "Identification of the Cystic Fibrosis Gene: Genetic Analysis" Science 1989 245:1073-1080.

Leach, A. R. and Lemon, A. P. "Exploring the Conformational Space of Protein Side Chains Using Dead-end Elimination and the A* Algorithm" Proteins: Structure, Function, and Genetics 1998 33:227-239.

Li, C. and Naren, A.P. "Macromolecular Complexes of Cystic Fibrosis Transmembrane Conductance Regulator and its Interacting Partners" Pharmacology & Therapeutics 2005 108(2):208-223.

Lukacs et al. "The ΔF508 Mutation Decreases the Stability of Cystic Fibrosis Transmembrane Conductance Regulator in the Plasma Membrane" The Journal of Biological Chemistry 1993 268(29):21592-21598.

Pedemonte et al. "Small-Molecule Correctors of Defective ΔF508-CFTR Cellular Processing Identified by High-Throughput Screening" The Journal of Clinical Investigation 2005 115(9):2564-2571.

Piserchio et al. "Association of the Cystic Fibrosis Transmembrane Regulator with CAL: Structural Features and Molecular Dynamics" Biochemistry 2005 44:16158-16166.

Que et al. "Improving Rate of Decline of $FEV_1$ in Young Adults with Cystic Fibrosis" Thorax 2006 61:155-157.

Ramsey et al. "A CFTR Potentiator in Patients with Cystic Fibrosis and the G551D Mutation" The New England Journal of Medicine 2011 365(18):1663-1672.

Reynolds et al. "Computational Redesign of the SHV-1 β-Lactamase/β-Lactamase Inhibitor Protein Interface" Journal of Molecular Biology 2008 382:1265-1275.

Riordan, J. R. "CFTR Function and Prospects for Therapy" Annual Review of Biochemistry 2008 77:701-726.

Schulz et al. "Immunocytochemical Detection of Somatostatin Receptors sst1, sst2A, sst2B, and sst3 in Paraffin-Embedded Breast Cancer Tissue Using Subtype-Specific Antibodies" Clinical Cancer Research 1998 4(9):2047-2052.

Taylor-Robinson et al. "Understanding the Natural Progression in %$FEV_1$ Decline in Patients with Cystic Fibrosis: A Longitudinal Study" Thorax 2012 67:860-866.

Van Goor et al. "Correction of the F508del-CFTR Protein Processing Defect In Vitro by the Investigational Drug VX-809" Proceedings of the National Academy of Sciences 2011 108(46):18843-18848.

Van Goor et al. "VX-809, A CFTR Corrector, Increases the Cell Surface Density of Functional F508del-CFTR in Pre-Clinical Models of Cystic Fibrosis" The $23^{rd}$ Annual North American Cystic Fibrosis Conference 2009 S9.4:154-155.

Wolde et al. "Targeting CAL as Negative Regulator of ΔF508-CFTR Cell-Surface Expression" The Journal of Biological Chemistry 2007 282(11):8099-8109.

Yamada et al. "Conformation of the Transmembrane Domains in Peripheral Myelin Protein 22. Part 1. Solution-Phase Synthesis and Circular Dichroism Study of Protected 17-Residue Partial Peptides in the First Putative Transmembrane Domain" The Journal of Peptide Research 2003 62:78-87.

Office Communication dated Jul. 23, 2012 from U.S. Appl. No. 13/124,470, filed Apr. 15, 2011.

Office Communication dated Aug. 28, 2013 from U.S. Appl. No. 13/292,151, filed Nov. 9, 2011.

Office Communication dated Feb. 13, 2015 from U.S. Appl. No. 14/105,646, filed Dec. 13, 2013.

International Search Report from PCT/US2009/061246, dated Aug. 25, 2010, PCT.

International Preliminary Report on Patentability from PCT/US2009/061246, dated May 5, 2011, PCT.

International Search Report from PCT/US2012/063486, dated Mar. 15, 2013, PCT.

International Search Report and Written Opinion in PCT/US2016/033476 dated Oct. 4, 2016.

International Preliminary Report on Patentability in PCT/ US2016/033476 dated Nov. 28, 2017.

Office communication dated May 19, 2016 from U.S. Appl. No. 14/719,910, filed May 22, 2015.

* cited by examiner

SEQUENCE LISTING

<160> NUMBER OF SEQ ID NOS: 38

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide.

<400> SEQUENCE: 1

Ala Asn Ser Arg Trp Pro Thr Ser Ile Ile
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide.

<400> SEQUENCE: 2

Ala Asn Ser Arg Leu Pro Thr Ser Ile Ile
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION

<400> SEQUENCE: 3

Trp Gln Val Thr Arg Val
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (1)..(1)
<223> OTHER INFORMATION: Xaa denotes Met; Phe; Leu; Ala; Trp; Dbu; Dpa
      or Formula I.
<220> FEATURE:
<221> NAME/KEY: MISC_FEATURE
<222> LOCATION: (2)..(2)
<223> OTHER INFORMATION: Xaa denotes Gln; Pro; Phe; S-pipecolic acid or
      Formula II.
<220> FEATURE:
<221> NAME/KEY: MISC_FEATURE
<222> LOCATION: (3)..(3)
<223> OTHER INFORMATION: Xaa denotes Ser; Val; Thr; or Formula III.
<220> FEATURE:
<221> NAME/KEY: MISC_FEATURE
<222> LOCATION: (4)..(4)
<223> OTHER INFORMATION: Xaa denotes Ser; Thr; or Formula IV.
<220> FEATURE:
<221> NAME/KEY: MISC_FEATURE
<222> LOCATION: (5)..(5)
<223> OTHER INFORMATION: Xaa denotes Lys; Arg; Ile; or Formula V.
<220> FEATURE:
<221> NAME/KEY: MISC_FEATURE
<222> LOCATION: (6)..(6)
<223> OTHER INFORMATION: Xaa denotes Ile; Val; tert-butyl glycine;
      tert-butyl alanine or Formula VI.

```
<400> SEQUENCE: 4

Xaa Xaa Xaa Xaa Xaa Xaa
1               5

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide.

<400> SEQUENCE: 5

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide.

<400> SEQUENCE: 6

Arg Arg Arg Arg Arg Arg Arg Arg
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic Peptide.

<400> SEQUENCE: 7

Gly Arg Lys Lys Arg Arg Gln Arg Arg Arg Pro Pro Gln Gln
1               5                   10

<210> SEQ ID NO 8
<211> LENGTH: 27
<212> TYPE: PRT
<213> ORGANISM: Artificial Sequence
<220> FEATURE:
<223> OTHER INFORMATION: Synthetic Peptide.

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 21
<212> TYPE: PRT
<213> ORGANISM: Artificial Sequence
<220> FEATURE:
<223> OTHER INFORMATION: Synthetic Peptide.

<400> SEQUENCE: 9

Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 10
<211> LENGTH: 18
<212> TYPE: PRT
<213> ORGANISM: Artificial Sequence
<220> FEATURE:
<223> OTHER INFORMATION: Synthetic Peptide.

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
<211> LENGTH: 27
<212> TYPE: PRT
<213> ORGANISM: Artificial Sequence
<220> FEATURE:
<223> OTHER INFORMATION: Synthetic Peptide.

<400> SEQUENCE: 11

Gly Ala Leu Phe Leu Ala Phe Leu Ala Ala Ala Leu Ser Leu Met Gly
1               5                   10                  15

Leu Trp Ser Gln Pro Lys Lys Lys Arg Lys Val
            20                  25

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.

<400> SEQUENCE: 13

Xaa Pro Val Thr Arg Val
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (2)..(2)
<223> OTHER INFORMATION: Xaa denotes denotes S-pipecolic acid.

<400> SEQUENCE: 14

Xaa Xaa Val Thr Arg Val
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (2)..(2)
<223> OTHER INFORMATION: Xaa denotes S-pipecolic acid.
<220> FEATURE:
<221> NAME/KEY: MISC_FEATURE
<222> LOCATION: (5)..(5)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (6)..(6)
<223> OTHER INFORMATION: Xaa denotes Gly with tert-butyl group; Ala with
      tert-butyl group; or Val with tert-butyl group.

<400> SEQUENCE: 15

Xaa Xaa Val Thr Xaa Xaa
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (2)..(2)
<223> OTHER INFORMATION: Xaa denotes S-pipecolic acid.
```

```
<220> FEATURE:
<221> NAME/KEY: MISC_FEATURE
<222> LOCATION: (3)..(3)
<223> OTHER INFORMATION: Xaa denotes Dpr; Dbu; Orn; Lys; mono- or
      dimethylated Dpr; mono- or dimethylated Dbu; mono- or dimethylated
      Orn; or mono- or dimethylated Lys.
<220> FEATURE:
<221> NAME/KEY: MISC_FEATURE
<222> LOCATION: (5)..(5)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (6)..(6)
<223> OTHER INFORMATION: Xaa denotes Gly with tert-butyl group; Ala with
      tert-butyl group; or Val with tert-butyl group.

<400> SEQUENCE: 16

Xaa Xaa Xaa Thr Xaa Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (2)..(2)
<223> OTHER INFORMATION: Xaa denotes S-pipecolic acid.
<220> FEATURE:
<221> NAME/KEY: MISC_FEATURE
<222> LOCATION: (3)..(3)
<223> OTHER INFORMATION: Xaa denotes Dpr; Dbu; Orn; Lys; mono- or
      dimethylated Dpr; mono- or dimethylated Dbu; mono- or dimethylated
      Orn; or mono- or dimethylated Lys.
<220> FEATURE:
<221> NAME/KEY: MISC_FEATURE
<222> LOCATION: (4)..(4)
<223> OTHER INFORMATION: Xaa denotes 3-hydroxyvaline; or Ser or Thr
      derivative including a beta carbon methyl, amino, cyano, halo,
      nitro, mercapto or phosphate group.
<220> FEATURE:
<221> NAME/KEY: MISC_FEATURE
<222> LOCATION: (5)..(5)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (6)..(6)
<223> OTHER INFORMATION: Xaa denotes Gly with tert-butyl group; Ala with
      tert-butyl group; or Val with tert-butyl group.

<400> SEQUENCE: 17

Xaa Xaa Xaa Xaa Xaa Xaa
1               5

<210> SEQ ID NO 18
<211> LENGTH: 6
<212> TYPE: PRT
<213> ORGANISM: Artificial Sequence
```

```
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (3)..(3)
<223> OTHER INFORMATION: Xaa denotes Dpr; Dbu; Orn; Lys; mono- or
      dimethylated Dpr; mono- or dimethylated Dbu; mono- or dimethylated
      Orn; or mono- or dimethylated Lys.
<220> FEATURE:
<221> NAME/KEY: MISC_FEATURE
<222> LOCATION: (4)..(4)
<223> OTHER INFORMATION: Xaa denotes 3-hydroxyvaline; or Ser or Thr
      derivative including a beta carbon methyl, amino, cyano, halo,
      nitro, mercapto or phosphate group.
<220> FEATURE:
<221> NAME/KEY: MISC_FEATURE
<222> LOCATION: (5)..(5)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (6)..(6)
<223> OTHER INFORMATION: Xaa denotes Gly with tert-butyl group; Ala with
      tert-butyl group; or Val with tert-butyl group.

<400> SEQUENCE: 18

Xaa Pro Xaa Xaa Xaa Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (4)..(4)
<223> OTHER INFORMATION: Xaa denotes 3-hydroxyvaline; or Ser or Thr
      derivative including a beta carbon methyl, amino, cyano, halo,
      nitro, mercapto or phosphate group.
<220> FEATURE:
<221> NAME/KEY: MISC_FEATURE
<222> LOCATION: (5)..(5)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (6)..(6)
<223> OTHER INFORMATION: Xaa denotes Gly with tert-butyl group; Ala with
      tert-butyl group; or Val with tert-butyl group.

<400> SEQUENCE: 19
```

```
Xaa Pro Val Xaa Xaa Xaa
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (6)..(6)
<223> OTHER INFORMATION: Xaa denotes S-pipecolic acid.

<400> SEQUENCE: 20

Ala Asn Ser Arg Trp Xaa Val Thr Arg Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (6)..(6)
<223> OTHER INFORMATION: Xaa denotes S-pipecolic acid.
<220> FEATURE:
<221> NAME/KEY: MISC_FEATURE
<222> LOCATION: (9)..(9)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (10)..(10)
<223> OTHER INFORMATION: Xaa denotes Gly with tert-butyl group; Ala with
      tert-butyl group; or Val with tert-butyl group.

<400> SEQUENCE: 21

Ala Asn Ser Arg Trp Xaa Val Thr Xaa Xaa
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (5)..(5)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (6)..(6)
<223> OTHER INFORMATION: Xaa denotes S-pipecolic acid.
<220> FEATURE:
<221> NAME/KEY: MISC_FEATURE
<222> LOCATION: (7)..(7)
<223> OTHER INFORMATION: Xaa denotes Dpr; Dbu; Orn; Lys; mono- or
      dimethylated Dpr; mono- or dimethylated Dbu; mono- or dimethylated
      Orn; or mono- or dimethylated Lys.

<400> SEQUENCE: 22

Ala Asn Ser Arg Xaa Xaa Xaa Thr Arg Val
1               5                   10
```

```
<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (5)..(5)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (6)..(6)
<223> OTHER INFORMATION: Xaa denotes S-pipecolic acid.
<220> FEATURE:
<221> NAME/KEY: MISC_FEATURE
<222> LOCATION: (7)..(7)
<223> OTHER INFORMATION: Xaa denotes Dpr; Dbu; Orn; Lys; mono- or
      dimethylated Dpr; mono- or dimethylated Dbu; mono- or dimethylated
      Orn; or mono- or dimethylated Lys.
<220> FEATURE:
<221> NAME/KEY: MISC_FEATURE
<222> LOCATION: (8)..(8)
<223> OTHER INFORMATION: Xaa denotes 3-hydroxyvaline; or Ser or Thr
      derivative including a beta carbon methyl, amino, cyano, halo,
      nitro, mercapto or phosphate group.

<400> SEQUENCE: 23

Ala Asn Ser Arg Xaa Xaa Xaa Xaa Arg Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (9)..(9)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.

<400> SEQUENCE: 24

Ala Asn Ser Arg Leu Pro Thr Ser Xaa Ile
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (8)..(8)
<223> OTHER INFORMATION: Xaa denotes 3-hydroxyvaline; or Ser or Thr
      derivative including a beta carbon methyl, amino, cyano, halo,
      nitro, mercapto or phosphate group.
<220> FEATURE:
<221> NAME/KEY: MISC_FEATURE
<222> LOCATION: (9)..(9)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.

<400> SEQUENCE: 25

Ala Asn Ser Arg Leu Pro Thr Xaa Xaa Ile
1               5                   10
```

```
<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (10)..(10)
<223> OTHER INFORMATION: Xaa denotes Gly with tert-butyl group; Ala with
      tert-butyl group; or Val with tert-butyl group.

<400> SEQUENCE: 26

Ala Asn Ser Arg Trp Gln Val Thr Arg Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (5)..(5)
<223> OTHER INFORMATION: Xaa denotes Dpr; Dbu; Orn or Lys coupled to a
      mono-, di-, tri- or tetra-tert-butyl substituted 1H-indole-2-
      carboxylic acid; or Trp substituted with one or more tert-butyl
      substituents.
<220> FEATURE:
<221> NAME/KEY: MISC_FEATURE
<222> LOCATION: (6)..(6)
<223> OTHER INFORMATION: Xaa denotes S-pipecolic acid.
<220> FEATURE:
<221> NAME/KEY: MISC_FEATURE
<222> LOCATION: (7)..(7)
<223> OTHER INFORMATION: Xaa denotes Dpr; Dbu; Orn; Lys; mono- or
      dimethylated Dpr; mono- or dimethylated Dbu; mono- or dimethylated
      Orn; or mono- or dimethylated Lys.
<220> FEATURE:
<221> NAME/KEY: MISC_FEATURE
<222> LOCATION: (8)..(8)
<223> OTHER INFORMATION: Xaa denotes 3-hydroxyvaline; or Ser or Thr
      derivative including a beta carbon methyl, amino, cyano, halo,
      nitro, mercapto or phosphate group.
<220> FEATURE:
<221> NAME/KEY: MISC_FEATURE
<222> LOCATION: (9)..(9)
<223> OTHER INFORMATION: Xaa denotes Lys coupled to aminoethyl benzoic
      acid; or Dpr, Dbu or Orn coupled to a substituted aryl,
      heteroaryl, cycloalky or heterocycloalkyl.
<220> FEATURE:
<221> NAME/KEY: MISC_FEATURE
<222> LOCATION: (10)..(10)
<223> OTHER INFORMATION: Xaa denotes Gly with tert-butyl group; Ala with
      tert-butyl group; or Val with tert-butyl group.

<400> SEQUENCE: 27

Ala Asn Ser Arg Xaa Xaa Xaa Xaa Xaa Xaa
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (1)..(1)
<223> OTHER INFORMATION: Xaa denotes Leu or Trp.
<220> FEATURE:
<221> NAME/KEY: MISC_FEATURE
```

```
<222> LOCATION: (2)..(2)
<223> OTHER INFORMATION: Xaa denotes Gln or Pro.
<220> FEATURE:
<221> NAME/KEY: MISC_FEATURE
<222> LOCATION: (3)..(3)
<223> OTHER INFORMATION: Xaa denotes Val or Thr.
<220> FEATURE:
<221> NAME/KEY: MISC_FEATURE
<222> LOCATION: (4)..(4)
<223> OTHER INFORMATION: Xaa denotes Ser or Thr.
<220> FEATURE:
<221> NAME/KEY: MISC_FEATURE
<222> LOCATION: (5)..(5)
<223> OTHER INFORMATION: Xaa denotes Arg or Ile.
<220> FEATURE:
<221> NAME/KEY: MISC_FEATURE
<222> LOCATION: (6)..(6)
<223> OTHER INFORMATION: Xaa denotes Ile or Val.

<400> SEQUENCE: 28

Xaa Xaa Xaa Xaa Xaa Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION

<400> SEQUENCE: 29

Trp Pro Val Thr Arg Val
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION

<400> SEQUENCE: 30

Leu Pro Val Thr Arg Val
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa denotes diaminopropionic acid coupled to
      6-tert-butyl-1-H-indole-2-carboxylic acid.

<400> SEQUENCE: 31

Xaa Pro Val Thr Arg Val
1               5
```

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide.

<400> SEQUENCE: 32

Ala Asn Ser Arg Trp Gln Val Thr Arg Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (6)..(6)
<223> OTHER INFORMATION: Xaa denotes S-pipecolic acid.

<400> SEQUENCE: 33

Ala Asn Ser Arg Trp Xaa Val Thr Arg Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MOD_RES
<222> LOCATION: (9)..(9)
<223> OTHER INFORMATION: ACETYLATION

<400> SEQUENCE: 34

Ala Asn Ser Arg Leu Pro Thr Ser Lys Ile
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (9)..(9)
<223> OTHER INFORMATION: Coupled to aminoethyl benzoic acid.

<400> SEQUENCE: 35

Ala Asn Ser Arg Leu Pro Thr Ser Lys Ile
1               5                   10

```
<210> SEQ ID NO 36
<211> LENGTH: 10
<212> TYPE: PRT
<213> ORGANISM: Artificial Sequence
<220> FEATURE:
<223> OTHER INFORMATION: Synthetic Peptide.

<400> SEQUENCE: 36

Ala Asn Ser Arg Trp Gln Val Thr Arg Val
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (10)..(10)
<223> OTHER INFORMATION: Xaa denotes tert-butyl glycine.

<400> SEQUENCE: 37

Ala Asn Ser Arg Trp Gln Val Thr Arg Xaa
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (5)..(5)
<223> OTHER INFORMATION: Xaa denotes diaminoproprionic acid coupled to
      6-tert-butyl-1-H-indole-2-carboxylic acid.
<220> FEATURE:
<221> NAME/KEY: MISC_FEATURE
<222> LOCATION: (6)..(6)
<223> OTHER INFORMATION: Xaa denotes S-pipecolic acid.
<220> FEATURE:
<221> NAME/KEY: MISC_FEATURE
<222> LOCATION: (7)..(7)
<223> OTHER INFORMATION: Xaa denotes diaminopropionic acid or
      diaminobutyric acid.
<220> FEATURE:
<221> NAME/KEY: MISC_FEATURE
<222> LOCATION: (8)..(8)
<223> OTHER INFORMATION: Xaa denotes 3-hydroxyvaline.
<220> FEATURE:
<221> NAME/KEY: MISC_FEATURE
<222> LOCATION: (9)..(9)
<223> OTHER INFORMATION: Coupled to aminoethyl benzoic acid.
<220> FEATURE:
<221> NAME/KEY: MISC_FEATURE
<222> LOCATION: (10)..(10)
<223> OTHER INFORMATION: Xaa denotes tert-butyl glycine.

<400> SEQUENCE: 38

Ala Asn Ser Arg Xaa Xaa Xaa Xaa Lys Xaa
1               5                   10
```

THERAPY AND KIT FOR THE PREVENTION AND TREATMENT OF CYSTIC FIBROSIS

This application claims benefit of priority of U.S. 62/506,952, filed May 16, 2017, and is a continuation-in-part application of PCT/US2016/033476, filed May 20, 2016, which claims benefit of priority of U.S. patent application Ser. No. 14/719,910, filed May 22, 2015, the contents of which are incorporated herein by reference in their entireties.

This invention was made with government support under grant numbers R01-DK101451 and T32-GM008704 awarded by the National Institutes of Health. The government has certain rights in the invention.

INTRODUCTION

Background

CFTR (Cystic Fibrosis Transmembrane Conductance Regulator) is the target of mutations that cause cystic fibrosis (CF). CF is characterized by abnormal endocrine and exocrine gland function. In CF, unusually thick mucus leads to chronic pulmonary disease and respiratory infections, insufficient pancreatic and digestive function, and abnormally concentrated sweat. Seventy percent of the mutant CFTR alleles in the Caucasian population result from deletion of phenylalanine at position 508 (ΔF508-CFTR), the result of a three base pair deletion in the genetic code. Other mutations have also been described, e.g., a glycine to aspartate substitution at position 551 (G551D-CFTR) occurs in approximately 3-4% of cystic fibrosis patients.

The ΔF508-CFTR mutation results in a CFTR protein capable of conducting chloride, but absent from the plasma membrane because of aberrant intracellular processing. Under usual conditions (37° C.), the ΔF508-CFTR protein is retained in the endoplasmic reticulum (ER), by prolonged association with the ER chaperones, including calnexin and hsp70. Over expression of ΔF508-CFTR can result in ΔF508-CFTR protein appearing at the cell surface, and this protein is functional once it reaches the cell surface. The ΔF508-CFTR "trafficking" block is also reversible by incubation of cultured CF epithelial cells at reduced temperatures (25-27° C.). Lowered temperature results in the appearance of CFTR protein and channel activity at the cell surface, suggesting an intrinsic thermodynamic instability in ΔF508-CFTR at 37° C. that leads to recognition of the mutant protein by the ER quality control mechanism, prevents further trafficking, and results in protein degradation. Chemical chaperones are currently being developed to restore the folding of ΔF508-CFTR. However, when ΔF508-CFTR is expressed at the cell-surface following treatment, CAL (also known as CFTR-associated ligand, PIST, GOPC, ROS, and FIG) directs the lysosomal degradation of CFTR in a dose-dependent fashion and reduces the amount of CFTR found at the cell surface. Conversely, NHERF1 and NHERF2 functionally stabilize CFTR. Consistent with this role of CAL, RNA interference targeting of endogenous CAL also increases cell-surface expression of the disease-associated ΔF508-CFTR mutant and enhances transepithelial chloride currents in a polarized human patient bronchial epithelial cell line.

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, and restoration of the expression of functional CFTR at the cell surface is considered a major therapeutic goal in the treatment of cystic fibrosis, a disease that affects ~30,000 patients in the U.S., and 70,000 patients worldwide. For example, KALYDECO (Ivacaftor; VX-770) is an FDA-approved compound that 'potentiates' the open probability ($P_o$) of CFTR channels, including the G551D mutant, and thus ameliorates the underlying molecular lesion in this group of patients. A 48-week clinical trial showed excellent efficacy, including a 10.6% improvement in lung function (predicted forced expiratory volume in 1 second; FEV1), a 55% drop in pulmonary exacerbations, and a 48 mEq/L reduction in sweat chloride (Ramsey, et al. (2011) *N. Engl. J. Med.* 365:1663-72). While showing efficacy in subjects with the G551D mutation, KALYDECO is not useful as a monotherapy for the largest group of CF patients. In ~70% of mutant alleles, Phe508 is deleted (ΔF508; Kerem, et al. (1989) *Science* 245: 1073-1080). As a result, ~50% of CF patients are ΔF508 homozygous and ~40% are heterozygous. Unfortunately, clinical trials in ΔF508 homozygotes show low efficacy for KALYDECO alone (Flume, et al. (2012) *Chest* 142:718-724).

In the absence of interventions, ΔF508-CFTR exhibits three defects: folding, gating, and stability. However, if folding is restored, ΔF508-CFTR retains some channel activity. 'Corrector' compounds have been identified such as corr-4a (Pedemonte et al. (2005) *J. Clin. Invest.* 115:2564) and Lumacaftor (VX-809), which partially alleviate the folding defect and allows some ΔF508-CFTR to reach the apical membrane (Van Goor, et al. (2009) *Pediatr. Pulmonol.* 44:S154-S155; Van Goor, et al. (2011) *Proc. Natl. Acad. Sci. USA* 108:18843-18848). Although Lumacaftor yields only limited benefits in monotherapy, it shows greater efficacy in combination with KALYDECO: 25% of patients showed a >10% increase in FEV1 and 55% of patients showed >5% increase, with few adverse effects. While a 5% or 10% improvement is clinically meaningful, $FEV_1$ drops approximately 1-2% per year in CF patients (Dasenbrook, et al. (2008) *Am. J. Respir. Crit. Care Med.* 178:814-821; Que, et al. (2006) *Thorax* 61:155-157), even in the absence of acceleration by pulmonary exacerbations (Taylor-Robinson, et al. (2012) *Thorax* 67:860-866). Thus, further improvements are required, especially for non-responders and the 40% of ΔF508-CFTR heterozygous patients.

The expression and function of the CFTR is regulated, in part, by the interaction with the PDZ domain of the CFTR-associated ligand (CAL). Competitive inhibition of this interaction increases the stability and function of CFTR in Cystic Fibrosis Bronchial Epithelial (CFBE) cells and represents an additional strategy for the treatment of CF. Peptide-based inhibitors of CAL PDZ, including iCAL36 (ANSRLPTSII; SEQ ID NO:1), iCAL42 (ANSRLPTSII; SEQ ID NO:2), and kCAL01 (Ac-WQVTRV; SEQ ID NO:3) have been described. See U.S. Pat. Nos. 8,415,292; 8,999,919 and 9,333,235. However, these peptides exhibit suboptimal affinity and/or specificity ($K_i$=~1 µM for kCAL01 peptide and $K_i$=~37 µM for the selective iCAL42 peptide) and substitution with natural amino acids yields a tradeoff between affinity and specificity for CAL PDZ.

SUMMARY OF THE INVENTION

The present invention is a peptidomimetic including the sequence of SEQ ID NO:4, or a derivative thereof (e.g., including a label, one or more post-translational modifications, and/or a cell-penetrating sequence). A pharmaceutical composition and kit including the peptidomimetic, either alone or in combination with a CFTR corrector, CFTR potentiator, mucolytic, anti-inflammatory agent or a combination thereof is also provided, as is a method for preventing or treating cystic fibrosis by administering to a subject in need of treatment an effective amount of the peptidomimetic.

DETAILED DESCRIPTION OF THE INVENTION

A series of peptide or peptidomimetic inhibitors for CAL PDZ have now been identified that (a) exhibit significantly enhanced affinity for CAL PDZ, without loss of meaningful specificity against the biologically relevant PDZ domains of Na+/H+ Exchanger Regulatory Factor-1 (NHERF-1) and Tax-Interacting Protein-1 (TIP-1); and/or (b) significantly attenuate off-target interactions with NHERF-1 and TIP-1 while retaining affinity for CAL PDZ. Accordingly, inhibitors of the present invention find application in increasing the cell surface expression of degradation-prone CFTR proteins and in the treatment for CF. In particular, CAL inhibition is of use in combination therapies for reversing the ΔF508 stability defect.

As used herein, "cell surface expression" of a CFTR protein refers to CFTR protein which has been transported to the surface of a cell. In this regard, an agent that increases the cell surface expression of a CFTR protein refers to an agent that increases the amount of CFTR protein, which is present or detected at the plasma membrane of a cell, as compared to a cell which is not contacted with the agent.

Genetic, biochemical, and cell biological studies have revealed a complex network of protein-protein interactions that are required for correct CFTR trafficking, including a number of PDZ (PSD-95, discs-large, zonula occludens-1) proteins, which act as adaptor molecules, coupling CFTR to other components of the trafficking and localization machinery, and to other transmembrane channels and receptors (Kunzelmann (2001) *News Physiol. Sci.* 16:167-170; Guggino & Stanton (2006) *Nat. Rev. Mol. Cell Biol.* 7:426-436). Class I PDZ domains typically recognize C-terminal binding motifs characterized by the sequence -(Ser/Thr)-X-Φ-COOH (where Φ represents a hydrophobic side chain, and X represents any amino acid) (Harris & Lim (2001) *J. Cell Sci.* 114:3219-3231; Brône & Eggermont (2005) *Am. J. Physiol.* 288:C20-C29). The cytoplasmic C-terminus of CFTR satisfies the class I PDZ binding motif, ending in the sequence Thr-Arg-Leu (Hall, et al. (1998) *Proc. Natl. Acad. Sci. USA* 95:8496-8501; Short, et al. (1998) *J. Biol. Chem.* 273:19797-19801; Wang, et al. (1998) *FEBS Lett.* 427:103-108) and it has been demonstrated that CFTR C-terminal PDZ-binding motif controls retention of the protein at the apical membrane and modulates its endocytic recycling (Moyer, et al. (2000) *J. Biol. Chem.* 275:27069-27074; Swiatecka-Urban, et al. (2002) *J. Biol. Chem.* 277:40099-40105). PDZ proteins that have been shown to bind or interact with CFTR include NHERF1 (Na+/H+ exchanger regulatory factor 1; also known as EBP50), NHERF2 (Na+/H+ exchanger regulatory factor 2, also known as E3KARP), NHERF3 (Na+/H+ exchanger regulatory factor 3, also known as CAP70, PDZK1, or NaPi CAP-1), NHERF4 (Na+/H+ exchanger regulatory factor 4, also known as IKEPP or NaPi CAP-2), and CAL (CFTR-associated ligand; also known as PIST, GOPC, and FIG; GENBANK Accession Nos. NP_065132 and NP_001017408, incorporated herein by reference) (Guggino & Stanton (2006) supra; Li & Naren (2005) *Pharmacol. Ther.* 108:208-223). Of these proteins, CAL has been shown to reduce the levels of recombinant wild-type CFTR found in whole cell lysates and at the cell surface, whereas overexpression of NHERF1 together with CAL can block this effect on both wild-type and ΔF508-CFTR (Cheng, et al. (2002) *J. Biol. Chem.* 277:3520-3529; Guerra, et al. (2005) *J. Biol. Chem.* 280:40925-40933). Moreover, RNAi targeting of endogenous CAL specifically increases cell surface expression of the ΔF508-CFTR mutant protein and enhances transepithelial chloride currents in a polarized human patient bronchial epithelial cell line (Wolde, et al. (2007) *J. Biol. Chem.* 282:8099-8109). These data indicate that the PDZ proteins which interact with CFTR have opposing functions. Thus, targeting the interaction of CAL with CFTR can stabilize a mutant CFTR protein and facilitate cell surface expression of the same.

The CFTR protein and mutants thereof are well-known in the art and wild-type human CFTR is disclosed in GEN-BANK Accession No. NP_000483, incorporated herein by reference. Misfolding of mutant CFTR proteins has been shown to dramatically augment the ubiquitination susceptibility of the protein in post-Golgi compartments (Swiatecka-Urban, et al. (2005) *J. Biol. Chem.* 280:36762). Thus, for the purposes of the present invention, the term "degradation-prone" when used as a modifier of a CFTR protein, refers to a mutant CFTR protein that exhibits an increased rate of degradation following initial trafficking to the cell surface and a decrease in the amount of CFTR protein present at the cell surface (i.e., plasma membrane). Examples of degradation-prone CFTR proteins include, but are not limited to ΔF508 CFTR and Δ70F CFTR (see Sharma, et al. (2004) *J. Cell Biol.* 164:923). Other degradation-prone CFTR proteins are known in the art and/or can be identified by routine experimentation. For example, the rate or amount of transport of CFTR protein from the cell surface can be determined by detecting the amount of complex-glycosylated CFTR protein present at the cell surface, in endoplasmic vesicles and/or in lysosomes using methods such as cell surface immunoprecipitation or biotinylation or cell immunocytochemistry with an antibody specific for CFTR protein. Additional methods, both in vivo and in vitro, are known in the art that can be used for detecting an increase or decrease in cell surface expression of a CFTR protein.

Because PDZ proteins share overlapping specificities, particular embodiments of this invention embrace inhibitory agents that selectively block the interaction or binding between a degradation-prone CFTR and CAL. As used herein, a "selective inhibitor of the CFTR and CAL interaction" or "an agent that selectively inhibits the interaction between the degradation-prone CFTR and CAL" is any molecular species that is an inhibitor of the CFTR and CAL interaction but which fails to inhibit, or inhibits to a substantially lesser degree the interaction between CFTR and proteins that stabilize degradation-prone CFTR, e.g., NHERF1 AND NHERF2. Methods for assessing the selectively of an inhibitor of the CFTR and CAL interaction are disclosed herein and can be carried out in in vitro or in vivo assays.

As indicated, the present invention features compositions and methods for facilitating the cell surface expression of mutant CFTR by selectively blocking the interaction between a degradation-prone CFTR and CAL. In particular, the invention provides peptides or peptidomimetics that selectively inhibit the interaction between a degradation-prone CFTR and CAL and their use in compositions and methods for facilitating the cell surface expression of mutant CFTR and preventing or treating cystic fibrosis.

As used herein, the term "peptide" denotes a polymer composed of one or more amino acids. A "peptidomimetic" refers to a synthetic chemical compound which has substantially the same structural and/or functional characteristics of the peptides of the invention. Peptides or peptidomimetics of the present invention are desirably 6 to 20 residues in length, or more desirably 7 to 15 residues in length. Ideally, a selective inhibitor of the CFTR and CAL interaction is a 6 to 20 residue peptide or peptidomimetic including the common structure NH$_2$-Xaa$_1$-Xaa$_2$-Xaa$_3$-Xaa$_4$-Xaa$_5$-Xaa$_6$-COOH (SEQ ID NO:4), wherein:

(a) Xaa$_1$ is Met, Phe, Leu, Ala, Trp or a residue of Formula I;
(b) Xaa$_2$ is Gln, Pro, Phe or a residue of Formula II;
(c) Xaa$_3$ is Ser, Val, Thr, or a residue of Formula III;
(d) Xaa$_4$ is Ser, Thr or a residue of Formula IV;
(e) Xaa$_5$ is Lys, Arg, Ile or a residue of Formula V; and
(f) Xaa$_6$ is Ile, Val or a residue of Formula VI;

with the proviso that said peptide includes at least one of Formula I, Formula II, Formula III, Formula IV, Formula V, or Formula VI at the respective positions of Xaa$_1$, Xaa$_2$, Xaa$_3$, Xaa$_4$, Xaa$_5$, or Xaa$_6$.

Formula I in the peptidomimetic of this invention represents a diaminopropionic acid, diaminobutyric acid, ornithine or lysine residue coupled to a mono-, di-, tri-, or tetra-tert-butyl substituted 1H-indole-2-carboxylic acid; or a tryptophan derivative substituted with one or more tert-butyl substituents (e.g., 4-tert-butyl tryptophan, 5-tert-butyl tryptophan, etc.). Accordingly, Formula I has the following structure:

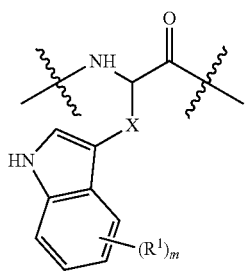

Formula I wherein X is —CH$_2$— or —(CH$_2$)$_n$—NH—; m is 1 to 4; n is 1 to 4; and each occurrence of R$^1$ is a tert-butyl group.

Formula II in the peptidomimetic of this invention represents pipecolic acid or a derivative thereof with one or more functional substituents (e.g., an amino group, hydroxyl group, or methyl group) at the C-3, C-4, C-5, or C-6 positions. Accordingly, Formula II has the following structure:

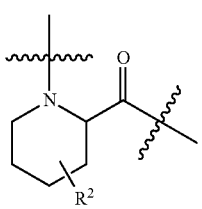

Formula II wherein R$^2$ is substituted at least one time anywhere on the ring and is a hydrogen, hydroxyl, methyl, amino, cyano, halo, nitro, mercapto, or phosphate group.

Formula III in the peptidomimetic of this invention represents diaminopropionic acid (DAP), diaminobutyric acid (DAB), ornithine, lysine or an analog thereof (e.g., mono- or dimethylated DAP, DAB, ornithine, or lysine). Accordingly, Formula III has the following structure:

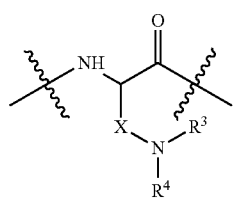

Formula III wherein X is —(CH$_2$)$_n$—; n is 1 to 4; and R$^3$ and R$^4$ are independently a hydrogen or methyl group.

Formula IV in the peptidomimetic of this invention represents 3-hydroxyvaline, and serine or threonine analogs containing a β carbon substituent. Accordingly, Formula IV has the following structure:

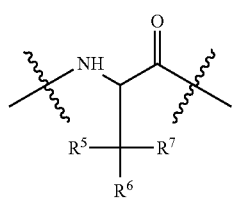

Formula IV wherein R$^5$, R$^6$ and R$^7$ are each independently a hydrogen, hydroxyl, methyl, amino, cyano, halo, nitro, mercapto, or phosphate group, with the proviso that at least one of R$^5$, R$^6$ or R$^7$ is a hydroxyl group.

Formula V in the peptidomimetic of this invention represents lysine coupled to aminoethyl benzoic acid, or diaminopropionic acid, diaminobutyric acid, or ornithine coupled to a substituted aryl, heteroaryl, cycloalkyl or heterocycloalkyl. Accordingly, Formula V has the following structure:

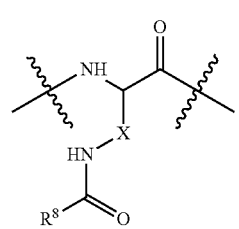

Formula V wherein X is —(CH$_2$)$_n$—; n is 1 to 4; and R$^8$ is a substituted aryl, heteroaryl, cycloalkyl or heterocycloalkyl.

As used herein, the term "aryl" refers to a radical, having a single carbon atom as point of attachment, wherein the carbon atom is part of an aromatic ring structure containing only carbon atoms. Unless otherwise indicated, aryls of the invention have between 5 and 7 carbon atoms, preferably 6 carbon atoms.

The term "heteroaryl" refers to a monovalent group with an aromatic carbon atom as the point of attachment, said carbon atom forming part of an aromatic ring structure wherein at least one of the ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, and pyrroloimidazolyl.

"Cycloalkyl" means a non-aromatic preferably monocyclic ring including 5 to 7 carbon atoms, preferably 6 carbon atoms. Non-limiting examples of suitable monocyclic cycloalkyls include cyclopentyl, cyclohexyl, and cycloheptyl.

"Heterocycloalkyl" means a non-aromatic saturated monocyclic ring system including 5 to 7 carbon atoms, preferably 6 carbon atoms, in which one or more of the atoms in the ring system is an element other than carbon, for example nitrogen, oxygen or sulfur, alone or in combination. Non-limiting examples of suitable monocyclic heterocycloalkyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, tetrahydrothiophenyl, lactam, lactone, and the like.

The term "substituted," when used to modify aryl, heteroaryl, cycloalkyl and heterocycloalkyl, means that one or more hydrogens on the designated atom is replaced with a selection from the indicated group, provided that the designated atom's normal valency under the existing circumstances is not exceeded, and that the substitution results in a stable compound. Exemplary substituents include, but are not limited to, hydroxyl, amino, cyano, halo (e.g., trifluoro), nitro, mercapto, phosphate, —COOH, —CO$_2$Me, —CONH$_2$, —CH$_2$CH$_2$NH$_2$, or alkyl groups.

Any undefined valency on an atom of a structure shown in this application implicitly represents a hydrogen atom bonded to the atom.

Formula VI in the peptidomimetic of this invention represents amino acids such as glycine, alanine, valine and the like with tert-butyl groups. Accordingly, Formula VI has the following structure:

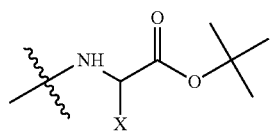

Formula VI wherein X is hydrogen or C$_{1-4}$ alkyl (e.g., methyl, ethyl, propyl, isopropyl, butyl, sec-butyl, isobutyl or tert-butyl).

In accordance with the present invention, a peptide or peptidomimetic of the invention can include an N-terminal, C-terminal, and/or one or more of the side chain chemical alterations or derivatizations. Such derivatizations include, for example, a label, such as fluorescein or tetramethylrhodamine; or one or more post-translational modifications such as acetylation, amidation, formylation, hydroxylation, methylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Brand, et al. (1996) *Am. J. Physiol. Cell. Physiol.* 270:C1362-C1369).

In addition, a derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245: 1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or peptidomimetic of the invention into the cell. Examples of known cell-penetrating peptides (CPP) are provided in Table 1.

TABLE 1

| CPP | Sequence | SEQ ID NO: |
|---|---|---|
| MPG | GALFLGFLGAAGSTMGAWSQPKKKRKV | 5 |
| R8 | RRRRRRRR | 6 |
| Tat (48-60) | GRKKRRQRRRPPQQ | 7 |
| Transportan | GWTLNSAGYLLGKINLKALAALAKKIL | 8 |
| TP10 | AGYLLGKINLKALAALAKKIL | 9 |
| MAP | KLALKLALKALKAALKLA | 10 |
| MPG-a | GALFLAFLAAALSLMGLWSQPKKKRKV | 11 |
| Penetratin | RQIKIWFQNRRMKWKK | 12 |

While a peptide or peptidomimetic of the invention can be derivatized with by one of the above indicated modifications, it is understood that a peptide or peptidomimetic of this invention may contain more than one of the above described modifications within the same molecule.

The peptidomimetic or mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit the interaction between CFTR and CAL. The phrase "substantially the same," when used in reference to a mimetic or peptidomimetic, means that the mimetic or peptidomimetic has one or more activities or functions of the referenced molecule, e.g., selective inhibition of the CAL and CFTR interaction.

There are advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, peptides described above have utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a CAL protein, by NMR spectroscopy, crystallography and/or computer-aided molecular modeling. These techniques aid in the development of novel compositions of higher potency and/or greater bioavailability and/or greater stability than the original peptide (Dean (1994) BioEssays 16:683-687; Cohen & Shatzmiller (1993) J. Mol. Graph. 11:166-173; Wiley & Rich (1993) Med. Res. Rev. 13:327-384; Moore (1994) Trends Pharmacol. Sci. 15:124-129; Hruby (1993) Biopolymers 33:1073-1082; Bugg, et al. (1993) Sci. Am. 269:92-98). Once a potential peptidomimetic compound is identified, it may be synthesized and assayed using an assay described herein or any other appropriate assay for monitoring cell surface expression of CFTR.

It will be readily apparent to one skilled in the art that a peptidomimetic can be generated from any of the peptides described herein. It will furthermore be apparent that the peptidomimetics of this invention can be further used for the development of even more potent non-peptidic compounds, in addition to their utility as therapeutic compounds.

Peptidomimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropyl-carbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—) thiazole, retroamide, thioamide, or ester (see, e.g., Spatola (1983) in Chemistry and Biochemistry of Amino Acids, Peptides and Proteins, 7:267-357, "Peptide and Backbone Modifications," Marcel Decker, NY).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues as mimetics of aromatic amino acids include, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenyl-phenylalanine; D- or L-p-methoxy-biphenyl-phenylalanine; and D- or L-2-indole(alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Cyclic peptides or cyclized residue side chains also decrease susceptibility of a peptide to proteolysis by exopeptidases or endopeptidases. Thus, certain embodiments embrace a peptidomimetic of the peptides disclosed herein, whereby one or more amino acid residue side chains are cyclized according to conventional methods.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N—C—N—R') including, for example, 1-cyclohexyl-3(2-morpholinyl-(4-ethyl) carbodiimide or 1-ethyl-3(4-azonia-4,4-dimetholpentyl) carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, dehydroproline, 3- or 4-methylproline, and 3,3-dimethylproline.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, the peptidomimetics of the present invention can include one or more of the modifications described herein for derivatized peptides, e.g., a label, one or more post-translational modifications, or cell-penetrating sequence.

In certain embodiments of the present invention, a selective inhibitor of the CFTR and CAL interaction is a peptide or peptidomimetic having a sequence as listed in Table 2.

TABLE 2

| Inhibitor | SEQ ID NO: |
| --- | --- |
| Ac-[Xaa$_1$] PVTRV | 13 |
| Ac-[Xaa$_1$] [Xaa$_2$] VTRV | 14 |
| Ac-[Xaa$_1$] [Xaa$_2$] VT [Xaa$_5$] [Xaa$_6$] | 15 |

TABLE 2-continued

| Inhibitor | SEQ ID NO: |
|---|---|
| Ac-[Xaa$_1$] [Xaa$_2$] [Xaa$_3$] T [Xaa$_5$] [Xaa$_6$] | 16 |
| Ac-[Xaa$_1$] [Xaa$_2$] [Xaa$_3$] [Xaa$_4$] [Xaa$_5$] [Xaa$_6$] | 17 |
| Ac-[Xaa$_1$] P [Xaa$_3$] [Xaa$_4$] [Xaa$_5$] [Xaa$_6$] | 18 |
| Ac-[Xaa$_1$] PV [Xaa$_4$] [Xaa$_5$] [Xaa$_6$] | 19 |
| ANSRW [Xaa$_2$] VTRV | 20 |
| ANSRW [Xaa$_2$] VT [Xaa$_5$] [Xaa$_6$] | 21 |
| ANSR [Xaa$_1$] [Xaa$_2$] [Xaa$_3$] TRV | 22 |
| ANSR [Xaa$_1$] [Xaa$_2$] [Xaa$_3$] [Xaa$_4$] RV | 23 |
| ANSRLPTS [Xaa$_5$] I | 24 |
| ANSRLPT [Xaa$_4$] [Xaa$_5$] I | 25 |
| ANSRWQVTR [Xaa$_6$] | 26 |
| ANSR [Xaa$_1$] [Xaa$_2$] [Xaa$_3$] [Xaa$_4$] [Xaa$_5$] [Xaa$_6$] | 27 |

Xaa$_1$ = Formula I;
Xaa$_2$ = Formula II;
Xaa$_3$ = Formula III;
Xaa$_4$ = Formula IV;
Xaa$_5$ = Formula V;
Xaa$_6$ = Formula VI;
Ac = acetylation.

Also included with the scope of the invention are peptides and peptidomimetics that are substantially identical to a sequence set forth herein. The term "substantially identical," when used in reference to a peptide or peptidomimetic, means that the sequence has at least 75% or more identity to a reference sequence (e.g., 80%, 85%, 90%, 95%, 96%, 97%, 98%, 99%). The length of comparison sequences will generally be at least 5 amino acids, but typically more, at least 6 to 10, 7 to 15, or 8 to 20 residues. In one aspect, the identity is over a defined sequence region, e.g., the amino or carboxy terminal 3 to 5 residues.

The peptides and peptidomimetics can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995) *Therapeutic Peptides and Proteins, Formulation, Processing and Delivery Systems*, Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes*, Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic Acids Res.* 25:3440-3444; Frenkel (1995) *Free Radic. Biol. Med.* 19:373-380; and Blommers (1994) *Biochemistry* 33:7886-7896).

Alternatively, peptides of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology* Vol. 182, Academic Press.

It is contemplated that the peptides and mimetics disclosed herein can be used as lead compounds for the design and synthesis of compounds with improved efficacy, clearance, half-lives, and the like. One approach includes structure-activity relationship (SAR) analysis (e.g., NMR analysis) to determine specific binding interactions between the agent and CAL or CFTR to facilitate the development of more efficacious agents. Agents identified in such SAR analysis or from agent libraries can then be screened for their ability to increase cell surface expression of CFTR.

In this regard, the present invention also relates to a method for identifying an agent for which facilitates cell surface expression of a degradation-prone CFTR. The method of the invention involves contacting CAL with a test agent under conditions allowing an interaction between the agent and CAL, and determining whether the agent competitively displaces binding of a degradation-prone CFTR to CAL. Particular degradation-prone CFTRs that can be used include, but are not limited to, ΔF508 and R1066C.

In one embodiment, the method is performed in vivo. Various detection methods can be employed to determine whether the agent displaces CFTR from CAL. For example, displacement can be based on detecting an increase in an amount of CFTR protein on the cell surface, immunostaining with a specific antibody (e.g., anti-CFTR, M3A7), or direct visualization (e.g., a CFTR-GFP fusion). Additional methods useful for determining whether there is an increase in cell surface protein included cell panning. In cell panning assays, plates are coated with an antibody that binds to the cell surface protein. The number of cells that binds to the antibody coated plate corresponds to an amount of protein on the cell surface.

In another embodiment, the method is performed in vitro. In accordance with this embodiment, a combination of peptide-array screening and fluorescence polarization is used to identify agents that bind to an isolated, recombinant CAL PZD domain. For example, it contemplated that the high-affinity CAL-binding peptides disclosed herein can be use as reporters for small-molecule screening assays, wherein the small molecules compete for binding to the CAL PZD domain. The ability to target PDZ proteins selectively, using a combination of peptide-array screening and fluorescence-polarization assays on purified, recombinant PDZ domains, represents a novel achievement, due to the bi-directional promiscuity of PDZ:protein interactions. Since PDZ proteins are implicated in the trafficking and intracellular localization of many disease-related receptors, selective targeting may provide an important tool for identifying additional PDZ-based therapeutics.

In so far as it is desirable that the agent selectively inhibits the interaction between CAL and CFTR, a further embodiment of this invention embraces contacting NHERF1 and/or NHERF2 with an identified inhibitor of the CAL and CFTR interaction and determining whether the agent competitively displaces binding to NHERF1 and/or NHERF2. Agents that fail to inhibit, or inhibit to a substantially lesser degree the interaction between CFTR and NHERF1 or NHERF2 as compared to CAL, would be considered selective.

Agents that can be screened in accordance with the methods disclosed herein can be from any chemical class including peptides, antibodies, small organic molecules, carbohydrates, etc.

Agents specifically disclosed herein, as well as derivatives, and peptidomimetics of said agents and agents identified by design and/or screening assays find application in increasing in the cell surface expression of degradation-prone CFTR proteins and in the treatment of CF. Thus, methods for increasing the cell surface expression of a degradation-prone CFTR and treating cystic fibrosis are also provided by this invention.

In accordance with one embodiment, the cell surface expression of a degradation-prone CFTR protein is enhanced or increased by contacting a cell expressing a degradation-prone CFTR with an agent that decreases or inhibits the interaction between the CFTR protein and CAL so that the cell surface expression of the CFTR protein is increased or enhanced. Desirably, the inhibitor is administered in an amount that effectively stabilizes the degradation-prone CFTR protein and increases the amount of said CFTR protein present or detectable at the cell surface by at least 60%, 70%, 80%, 90%, 95%, 99% or 100% as compared to cells not contacted with the agent. Any cell can be employed in this method of the invention so long as it expresses a degradation-prone CFTR. Specific examples of such cells include, but are not limited to, primary cells of a subject with CF or cultured airway epithelial cell lines derived from a CF patient's bronchial epithelium (e.g., CFBE41O–). It is contemplated that this method of the invention can be used to increase cell surface expression of a degradation-prone CFTR protein in a human subject as well as increase the cell surface expression of a degradation-prone CFTR protein in an isolated cell or cell culture to, e.g., study the transport and/or activity of the mutant protein at the cell surface.

In another embodiment, a subject with CF or at risk of CF is treated with one or more the inhibitors of the invention. In accordance with this embodiment, an effective amount of an agent that selectively inhibits the interaction between a degradation-prone CFTR and CAL is administered to a subject in need of treatment thereby preventing or treating the subject's cystic fibrosis. Subjects benefiting from treatment with an inhibitor of the invention include subjects confirmed as having CF, subjects suspected of having CF, or subjects at risk of having CF (e.g., subjects with a family history).

Cystic Fibrosis is known to result from the dysfunction of CFTR due to mutations in the gene. While the most common mutations involve a deletion of phenylalanine in position 508, other mutations have been described (Grasemann & Ratjen (2010) *Expert Opin. Emerg. Drugs.* 15:653-659; Pettit & Johnson (2011) *Ann. Pharmacother.* 45:49-59). These can be classified according to the effect they have on the CFTR (Table 3). In one aspect, the subject benefiting from treatment in accordance with the present invention expresses a degradation-prone CFTR (Class II mutation), such as ΔF508, ΔI507 or N1303K.

TABLE 3

| Class | Description |
|---|---|
| I | Defective or absence of CFTR protein synthesis with premature termination of CFTR production |
| II | Impaired processing: typically a defect in protein trafficking and degradation by the endoplasmic reticulum |
| III | Defective regulation: the CFTR reaches the apical cell surface but is not activated by ATP or cAMP |
| IV | Impaired function: transport of chloride ions is reduced at the apical membrane |
| V | Reduced synthesis of normal functioning CFTR |

Jones & Helm (2009) *Drugs* 69: 2003-2010; Grasemann & Ratjen (2010) *supra*; O'Sullivan & Freedman (2009) *Lancet* 373: 1991-2004.

Successful clinical use of an inhibitor of the invention can be determined by the skilled clinician based upon routine clinical practice, e.g., by monitoring frequency of respiratory infections and/or coughing; or changes in breathing, abdominal pain, appetite, and/or growth according to methods known in the art.

Inhibitors disclosed herein can be employed as isolated and purified molecules or be expressed from nucleic acids encoding said peptides. Such nucleic acids can, if desired, be naked or be in a carrier suitable for passing through a cell membrane (e.g., DNA-liposome complex), contained in a vector (e.g., plasmid, retroviral vector, lentiviral, adenoviral or adeno-associated viral vectors and the like), or linked to inert beads or other heterologous domains (e.g., antibodies, biotin, streptavidin, lectins, etc.), or other appropriate compositions. Thus, both viral and non-viral means of nucleic acid delivery can be achieved and are contemplated. Desirably, a vector used in accordance with the invention provides all the necessary control sequences to facilitate expression of the peptide. Such expression control sequences can include but are not limited to promoter sequences, enhancer sequences, etc. Such expression control sequences, vectors and the like are well-known and routinely employed by those skilled in the art.

For example, when using adenovirus expression vectors, the nucleic acid molecule encoding a peptide can be ligated to an adenovirus transcription/translation control complex, e.g., the late promoter and tripartite leader sequence. Alternatively, the vaccinia virus 7.5K promoter can be used. (see e.g., Mackett, et al. (1982) *Proc. Natl. Acad. Sci. USA* 79:7415-7419; Mackett, et al. (1984) *J. Virol.* 49:857-864; Panicali, et al. (1982) *Proc. Natl. Acad. Sci. USA* 79:4927-4931). Mammalian expression systems further include vectors specifically designed for "gene therapy" methods including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO 92/05266 and WO 92/14829).

In particular embodiments, the CFTR-CAL inhibitors of the invention are used in a combination therapy with at least one other agent employed in the treatment of cystic fibrosis, including molecules that ameliorate the signs or symptoms of cystic fibrosis. Other agents of use in the combination therapy include, but are not limited to CFTR correctors, CFTR potentiators, mucolytics and anti-inflammatory agents.

CFTR correctors are molecules that correct one or more defects found in Class II mutations by rescuing proteins from endoplasmic reticulum degradation, improving trafficking of CFTR to the cell surface, and/or inhibiting proteins that are involved in the recycling of CFTR in the cell membrane. Several correctors have been identified using high throughput assays (O'Sullivan & Freedman (2009) *Lancet* 373:1991-2004). For example, Ataluren (3-[5-(2-

Fluorophenyl)-1,2,4-oxadiazol-3-yl]benzoic acid) can cause ribosomal read-through of premature stop mutations in patients with class I mutations, correct the processing of CFTR, and thereby increase the production of functional CFTR (Jones & Helm (2009) supra; Wilschanski, et al. (2011) *Eur. Respir. J.* 38:59-69). Lumacaftor (VX-809; 3-{6-{[1-(2,2-difluoro-1,3-benzodioxol-5-yl)cyclopropanecarbonyl] amino}-3-methylpyridin-2-yl}benzoic acid) is another corrector that acts as a "chaperone" to assist the movement of defective CFTR to the epithelial cell membrane (Jones & Helm (2009) supra; O'Sullivan & Freedman (2009) supra). Indeed, it has been shown that Lumacaftor can restore the $P_o$ of ΔF508-CFTR to near wild-type levels (Van Goor, et al. (2011) supra). Lumacaftor can be provided in any suitable form including, but not limited to tablet, capsule, injectable, or aerosol. Dosing of Lumacaftor can be in the range of 200 to 600 mg once daily. Another corrector is corr-4a (N-(2-(5-Chloro-2-methoxy-phenylamino)-4'-methyl-[4,5']bithiazolyl-2'-yl)-benzamide), which increases F508Δ-CFTR cell-surface expression and increases chloride conductance. As demonstrated herein, iCAL36 peptide can enhance therapeutic efficacy of correctors such as corr-4a.

A CFTR potentiator enhances the activity of CFTR that is correctly located at the cell membrane. CFTR potentiators are particularly useful in the treatment of subjects with class III mutations. CFTR potentiators of use in this invention include certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl)isoxazole). Ivacaftor (VX-770; N-(2,4-Di-tert-butyl-5-hydroxyphenyl)-4-oxo-1,4-dihydroquinoline-3-carboxamide) has also been shown to increase CFTR channel open probability ($P_o$) in both the F508Δ processing mutation and the G551D gating mutation (Van Goor, et al. (2011) supra). Ivacaftor can be provided, e.g., in tablet form (KALYDECO; 150 mg Ivacaftor) or alternatively in any other suitable form, e.g., as an aerosol, capsule or injectable. Dosing of Ivacaftor can, e.g., include 250 mg Ivacaftor every 12 hours.

In some embodiments, the other agent is a single compound with dual corrector and potentiator activities. Such agents include VRT-532 (3-(2-hydroxy-5-methylphenyl)-5-phenylpyrazole) and cyanoquinolines such as N-(2-((3-Cyano-5,7-dimethylquinolin-2-yl)amino)ethyl)-3-methoxybenzamide (CoPo-2), as well as hybrid bithiazole-phenylglycine corrector-potentiators which, when cleaved by intestinal enzymes, yield an active bithiazole corrector and phenylglycine potentiator (Mills, et al. (2010) *Bioorg. Med. Chem. Lett.* 20:87-91).

Mucolytics are agents that dissolve thick mucus by dissolving various chemical bonds within secretions, which in turn can lower the viscosity by altering the mucin-containing components. Mucolytics of use in this invention include, but are not limited to acetylcysteine ((2R)-2-acetamido-3-sulfanylpropanoic acid), ambroxol (trans-4-(2-Amino-3,5-dibromobenzylamino)-cyclohexanol), bromhexine (2,4-dibromo-6-{[cyclohexyl(methyl)amino]methyl}aniline), carbocisteine (R)-2-Amino-3-(carboxymethylsulfanyl)propanoic acid), domiodol ([2-(iodomethyl)-1,3-dioxolan-4-yl]methanol), dornase alfa (recombinant human deoxyribonuclease I), eprazinone (3-[4-(2-ethoxy-2-phenyl-ethyl)piperazin-1-yl]-2-methyl-1-phenyl-propan-1-one), erdosteine (2-[(2-oxothiolan-3-yl)carbamoylmethylsulfanyl]acetic acid), letosteine (2-{2-[(2-ethoxy-2-oxoethyl)thio]ethyl}-1,3-thiazolidine-4-carboxylic acid), mannitol, mesna (sodium 2-sulfanylethanesulfonate), neltenexine (N-(2,4-dibromo-6-{[(4-hydroxycyclohexyl)amino]methyl}phenyl)thiophene-2-carboxamide), and sobrerol ((1S)-5-(1-hydroxy-1-methylethyl)-2-methylcyclohex-2-en-1-ol), stepronin (N-{2-[(2-thienylcarbonyl)thio]propanoyl}glycine).

Inflammation is a major component of cystic fibrosis. If untreated, inflammation can irreversibly damage the airways, leading to bronchiectasis and ultimately respiratory failure. Anti-inflammatory drugs used in the treatment of cystic fibrosis include steroids such as corticosteroids and nonsteroidal anti-inflammatory drugs such as ibuprofen. Other agents include pentoxifylline and azithromycin, which, in addition to its antimicrobial effects, also possesses anti-inflammatory properties.

Other therapeutics of use in combination with the agents of this invention include, but are not limited to, 2,2-dimethyl butyric acid (U.S. Pat. No. 7,265,153); glycerol, acetic acid, butyric acid, D- or L-amino-n-butyric acid, alpha- or beta-amino-n-butyric acid, arginine butyrate or isobutyramide, all disclosed in U.S. Pat. Nos. 4,822,821 and 5,025,029; and butyrin, 4-phenyl butyrate, phenylacetate, and phenoxy acetic acid, disclosed in U.S. Pat. No. 4,704,402.

The combination therapy of this invention preferably includes (a) at least one peptide or peptidomimetic that selectively inhibits the interaction between a degradation-prone CFTR and CAL and (b) a CFTR corrector, CFTR potentiator, mucolytic, anti-inflammatory agent, or combination thereof. In some embodiments, the combination therapy of this invention includes (a) at least one peptide or peptidomimetic that selectively inhibits the interaction between a degradation-prone CFTR and CAL and (b) a CFTR corrector, CFTR potentiator, or combination thereof. In accordance with this invention, the active agents of the combination therapy can be administered simultaneously of consecutively, within seconds, minutes, hours, days or weeks of each other. It is expected that the above-referenced combination therapy will have an additive or synergistic effect in the treatment of cystic fibrosis. In particular, it is expected that the combination of a selective inhibitor of the CFTR and CAL interaction, a CFTR corrector, and a CFTR potentiator will reverse all three defects (folding, gating, and stability) of ΔF508-CFTR.

The present invention also provides a kit containing (a) a peptide or peptidomimetic for inhibiting the interaction between a degradation-prone CFTR and CAL in combination with (b) a CFTR corrector, CFTR potentiator, mucolytic, anti-inflammatory agent, or combination thereof, for use in the prevention or treatment of cystic fibrosis. In some embodiments, the kit includes a plurality of separate containers, each containing at least one active agent useful in a combination therapy for the prevention or treatment of cystic fibrosis. The kit contains a first container containing a peptide or peptidomimetic for inhibiting the interaction between a degradation-prone CFTR and CAL. The kit further includes a container for a CFTR corrector, a container for a CFTR potentiator, a container for a mucolytic, and or a container for an anti-inflammatory agent. The containers of the kit may be enclosed within a common outer packaging, such as, for example a cardboard or plastic box or a shrink wrap outer skin enclosing the various containers. In certain embodiments, the peptide or peptidomimetic for inhibiting the interaction between a degradation-prone CFTR and CAL; and CFTR corrector, CFTR potentiator, mucolytic, and/or anti-inflammatory agent are each individually formulated in an acceptable carrier. The kit may be in the form of a consumer package or prescription package which provides the products described above. The package may provide instructions or directions on how to use and/or combine the products for one or more treatment regimens.

For therapeutic use, active agents of the invention can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols; such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically including via inhalation, transdermally, orally, intranasally, intravaginally, or rectally according to standard medical practices.

The selected dosage level of an agent will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician having ordinary skill in the art can readily determine and prescribe the effective amount of the pharmaceutical composition required based upon the administration of similar compounds or experimental determination. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The fact that other proteins destined for the intracellular transport pathway frequently exhibit transport delays due to mutations, or other factors, indicates that the cell-surface expression of such degradation-prone proteins may also be mediated by CAL. Thus, it is contemplated that the agents of this invention can also be used to induce or increase the cell surface expression of other degradation-prone proteins. Accordingly, physiological disorders associated with other degradation-prone proteins besides CFTR can similarly be treated using the methods disclosed herein. Physiological disorders associated with a degradation-prone protein that can be treated in a method of the invention include, for example, Stargardt's disease and particular types of macular dystrophy caused by mutations of the retinal rod transporter, ABC-R, resulting in deficiency of export.

The invention is described in greater detail by the following non-limiting examples.

Example 1: Peptidomimetics as Inhibitors of CAL PDZ

Peptide-based inhibitors of CAL PDZ, including iCAL36 (ANSRWPTSII; SEQ ID NO:1), iCAL42 (ANSRLPTSII; SEQ ID NO:2), and kCAL01 (Ac-WQVTRV; SEQ ID NO:3) have been described. See U.S. Pat. Nos. 8,415,292; 8,999,919 and 9,333,235. However, these peptides exhibit suboptimal affinity and/or specificity ($K_i$=~1 µM for kCAL01 peptide and $K_i$=~37 µM for the selective iCAL42 peptide) and substitution with natural amino acids yields a tradeoff between affinity and specificity for CAL PDZ. Accordingly, a series of modifications at each amino acid residue were carried out to identify inhibitors within increased affinity and/or specificity.

Collectively, iCAL36, iCAL42 and kCAL01 have the common structure: $Xaa_1$-$Xaa_2$-$Xaa_3$-$Xaa_4$-$Xaa_5$-$Xaa_6$ (SEQ ID NO:28), wherein $Xaa_1$ is Leu or Trp; $Xaa_2$ is Gln or Pro; $Xaa_3$ is Val or Thr; $Xaa_4$ is Ser or Thr; $Xaa_5$ is Arg or Ile; and $Xaa_6$ is Ile or Val. Notably, it has been found that substitution of Trp at $Xaa_1$ with diaminopropionic acid coupled to 6-tert-butyl-1-H-indole-2-carboxylic acid (DAP-BIC) confers a severe attenuation in binding for TIP-1 while retaining affinity for CAL PDZ. By comparison Leu at $Xaa_1$ confers increases selectivity but decreases affinity for CAL PDZ by 3-fold (Table 4). Further, substitution of Gln at $Xaa_2$ with S-pipecolic acid (PA) decreases binding for NHERF-1 PDZ1 (2.4-fold), NHERF-1 PDZ2 (4.2-fold), and TIP-1 (45-fold) while retaining affinity for CAL PDZ (Table 4). Of note, Pro at $Xaa_2$ confers selectivity but decreases affinity for CAL PDZ by 2-fold. Substitution of Ile at position $Xaa_5$ with lysine coupled to aminoethyl benzoic acid (K-AEBA) enhances affinity for CAL PDZ by 4.2-fold without loss of specificity. However, acetyl-lysine (Ac-K) at $Xaa_5$ (the control) results in no change in affinity for CAL PDZ (Table 4). In addition, substitution of Val at $Xaa_6$ with tert-butyl glycine (TBG) confers a 4-fold increase in affinity for CAL PDZ, no change in affinity for NHERF-1 PDZ1, and a 12-fold decrease in binding for TIP-1 (Table 4).

TABLE 4

| Peptide | SEQ ID NO: | $K_i$ (μM)* CAL PDZ | TIP-1 | NHERF-1 PDZ1 | NHERF-1 PDZ2 |
|---|---|---|---|---|---|
| Ac-WPVTRV | 29 | 1.22 ± 0.14[c] | 0.258 ± 0.044[c] | N.D. | N.D. |
| Ac-LPVTRV | 30 | 4.42 ± 0.97[c] | >5000[c] | N.D. | N.D. |
| Ac-[DAP-BIC] PVTRV | 31 | 1.87 ± 0.40[c] | 320 ± 300[c] | N.D. | N.D. |
| ANSRWQVTRV | 32 | 1.17 ± 0.06[b] | 0.057[a] | 2.80[a] | 207.7[a] |
| ANSRW [PA] VTRV | 33 | 1.36[a] | 2.59[a] | 6.81[a] | 865.4[a] |
| ANSRLPTSII | 2 | 36.6 ± 4.3[c] | >5000[c] | >5000[c] | >5000[c] |
| ANSRLPTS [Ac-K] I | 34 | 32.4 ± 10.5[c] | >5000[c] | >5000[c] | >5000[c] |
| ANSRLPTS [K-AEBA] I | 35 | 8.7 ± 0.9[c] | >5000[c] | >5000[c] | >5000[c] |
| ANSRWQVTRV | 36 | 1.13[a] | 0.057[a] | 2.80[a] | N.D. |
| ANSRWQVTR [TBG] | 37 | 0.23[a] | 0.70[a] | 2.97[a] | N.D. |

*All binding affinities were determined by competitive fluorescence polarization experiments.
[a]denotes n = 1;
[b]denotes n = 2;
[c]denotes n ≥ 3 for all experiments.
N.D., not determined.

Substitution of $Xaa_3$ with diaminopropionic acid (DAP) or diaminobutyric acid (DAB) is expected to improve affinity and specificity by forming multiple hydrogen bonds with the neighboring residues S302, T304, S316, and E317 of CAL PDZ. Moreover, substitution of $Xaa_4$ with 3-hydroxy-valine (3-HV) is expected to improve affinity and specificity by retaining the hydrogen bond with H349 of CAL PDZ while also forming hydrophobic interactions with I303 and V353.

In addition to diaminopropionic acid coupled to 6-tert-butyl-1-H-indole-2-carboxylic acid at $Xaa_1$, related linker residues such as diaminobutyric acid, ornithine or lysine coupled to isomers and related compounds of 6-tert-butyl-1-H-indole-2-carboxylic acid, e.g., an indole with single or multiple tert-butyl substituents at the C-4, C-5, C-6, or C-7 positions, are also contemplated at $Xaa_1$. Additionally, variations of $Xaa_1$ include tryptophan with single or multiple tert-butyl substituents at the C-4, C-5, C-6, or C-7 positions devoid of a linker residue (e.g., 4-tert-butyl tryptophan, 5-tert-butyl tryptophan, etc.).

Variations at $Xaa_2$ include all functional substituents at the C-3, C-4, C-5, or C-6 positions (amino group, hydroxyl group, methylation, etc).

Variations at $Xaa_3$ include any lysine analogs.

Variations of $Xaa_4$ include all serine and threonine analogs containing a β branch.

Variations of $Xaa_5$ include related linker residues (e.g., diaminopropionic acid, diaminobutyric acid, ornithine, etc), all possible functional groups at the terminus of the piperidine ring, and any functional substituents on the benzene or piperidine rings.

Variations of $Xaa_6$ include related compounds containing tert-butyl-containing R-groups (tert-butyl alanine, etc).

Such variations are expected to improve binding determinants for CAL PDZ, solubility, bioavailability, cell permeability, and/or pharmacokinetic properties.

A peptidomimetic having the structure of ANSR[DAP-BIC][PA][DAP/DAB][3-HV][K-AEBA][TBG] (SEQ ID NO:38) is expected to exhibit increased affinity for CAL PDZ (approximately 64-fold) and provide a therapeutic with enhanced efficacy in CF therapy.

Example 2: Assays for Assessing Activity of Selective Inhibitors

Agents of the present invention can be assayed for their ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing & Zehrahn (1951) Acta. Physiol. Scand. 23:110-127) or nasal potential difference measurements (see Knowles, et al. (1995) Hum. Gene Therapy 6:445-455). Within such assays, an agent that stimulates a statistically significant increase in chloride transport at a concentration of about 1-300 μM is said to stimulate chloride transport.

Within one in vitro assay, the level of chloride transport may be evaluated using mammalian pulmonary cell lines, such as Calu-3 cells, or primary bovine tracheal cultures. In general, such assays employ cell monolayers, which may be prepared by standard cell culture techniques. Within such systems, CFTR-mediated chloride current may be monitored in an Ussing chamber using intact epithelia. Alternatively, chloride transport may be evaluated using epithelial tissue in which the basolateral membrane is permeabilized with *Staphylococcus aureus* α-toxin, and in which a chloride gradient is imposed across the apical membrane (see Illek, et al. (1996) Am. J. Physiol. 270:C265-75). In either system, chloride transport is evaluated in the presence and absence of a test agent, and those compounds that stimulate chloride may be used within the methods provided herein.

Within another in vitro assay for evaluating chloride transport, cells, such as NIH 3T3 fibroblasts, are transfected with a CFTR gene having a mutation associated with cystic fibrosis (e.g., ΔF508-CFTR) using well known techniques (see Anderson, et al. (1991) Science 25:679-682). The effect of an agent on chloride transport in such cells is then evaluated by monitoring CFTR-mediated currents using the patch clamp method (see Hamill, et al. (1981) Pflugers Arch. 391:85-100) with and without agent.

Alternatively, such assays may be performed using a mammalian trachea, such as a primary cow tracheal epithelium using the Ussing chamber technique as described above. Such assays are performed in the presence and absence of a test agent to identify agents that stimulate chloride transport.

What is claimed is:

1. A peptidomimetic comprising the sequence NH$_2$-Xaa$_1$-Xaa$_2$-Xaa$_3$-Xaa$_4$-Xaa$_5$-Xaa$_6$ (SEQ ID NO:4), wherein:
   (i) Xaa$_1$ is Met, Phe, Leu, Ala, Trp, diaminobutyric acid, diaminopropionic acid or a residue of Formula I,

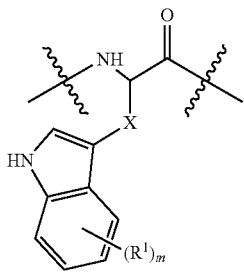

Formula I wherein X is —CH$_2$— or —(CH$_2$)$_n$—NH—, m is 1 to 4, n is 1 to 4, and each occurrence of R$^1$ is a tert-butyl group;
   (ii) Xaa$_2$ is Gln, Pro, Phe, S-pipecolic acid or a residue of Formula II,

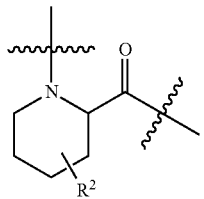

Formula II wherein R$^2$ is substituted at least one time anywhere on the ring and is a hydrogen, hydroxyl, methyl, amino, cyano, halo, nitro, mercapto, or phosphate group;
   (iii) Xaa$_3$ is Ser, Val, Thr or a residue of Formula III,

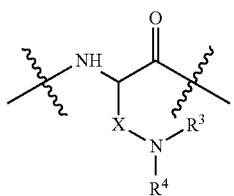

Formula III wherein X is —(CH$_2$)$_n$—, n is 1 to 4, and R$^3$ and R$^4$ are independently a hydrogen or methyl group;
   (iv) Xaa$_4$ is Ser, Thr or a residue of Formula IV,

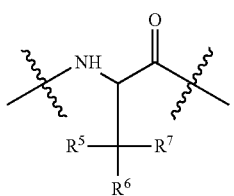

Formula IV wherein R$^5$, R$^6$ and R$^7$ are each independently a hydrogen, hydroxyl, methyl, amino, cyano, halo, nitro, mercapto, or phosphate group, with the proviso that at least one of R$^5$, R$^6$ or R$^7$ is a hydroxyl group;
   (v) Xaa$_5$ is Lys, Arg, Ile or a residue of Formula V,

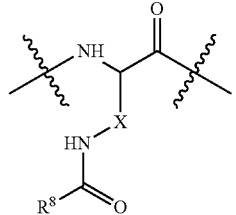

Formula V wherein X is —(CH$_2$)$_n$—, n is 1 to 4, and R$^8$ is a substituted aryl, heteroaryl, cycloalkyl or heterocycloalkyl; and
   (vi) Xaa$_6$ is Ile, Val, tert-butyl glycine and tert-butyl alanine or a residue of Formula VI,

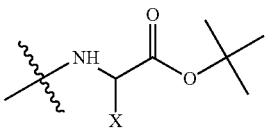

Formula VI wherein X is hydrogen or C$_{1-4}$ alkyl;
   with the proviso that the peptidomimetic includes at least one of Formula I, Formula II, Formula III, Formula IV, Formula V or Formula VI.

2. The peptidomimetic of claim 1, further comprising a label, one or more post-translational modifications, and/or a cell-penetrating sequence.

3. A pharmaceutical composition comprising the peptidomimetic of claim 1 in admixture with a pharmaceutically acceptable carrier.

4. The pharmaceutical composition of claim 3, further comprising a CFTR corrector, CFTR potentiator, mucolytic, anti-inflammatory agent or a combination thereof.

5. A kit comprising
   (a) peptidomimetic comprising the sequence NH$_2$-Xaa$_1$-Xaa$_2$-Xaa$_3$-Xaa$_4$-Xaa$_5$-Xaa$_6$ (SEQ ID NO:4), wherein:
      (i) Xaa$_1$ is Met, Phe, Leu, Ala, Trp, diaminobutyric acid, diaminopropionic acid or a residue of Formula I,

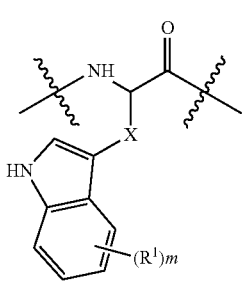

Formula I wherein X is —CH$_2$— or —(CH$_2$)$_n$—NH—, m is 1 to 4, n is 1 to 4, and each occurrence of R$^1$ is a tert-butyl group;
      (ii) Xaa$_2$ is Gln, Pro, Phe, S-pipecolic acid or a residue of Formula II, Formula II

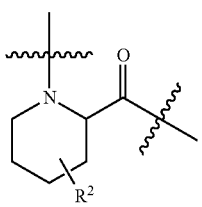

wherein R² is substituted at least one time anywhere on the ring and is a hydrogen, hydroxyl, methyl, amino, cyano, halo, nitro, mercapto, or phosphate group;

(iii) Xaa₃ is Ser, Val, Thr or a residue of Formula III,

Formula III

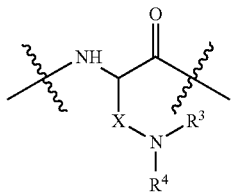

wherein X is —(CH₂)ₙ—, n is 1 to 4, and R³ and R⁴ are independently a hydrogen or methyl group;

(iv) Xaa₄ is Ser, Thr or a residue of Formula IV,

Formula IV

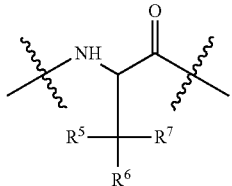

wherein R⁵, R⁶ and R⁷ are each independently a hydrogen, hydroxyl, methyl, amino, cyano, halo, nitro, mercapto, or phosphate group, with the proviso that at least one of R⁵, R⁶ or R⁷ is a hydroxyl group;

(v) Xaa₅ is Lys, Arg, Ile or a residue of Formula V,

Formula V

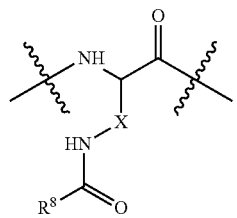

wherein X is —(CH₂)ₙ—, n is 1 to 4, and R⁵ is a substituted aryl, heteroaryl, cycloalkyl or heterocycloalkyl; and (vi) Xaa₆ is Ile, Val, tert-butyl glycine and tert-butyl alanine or a residue of Formula VI, Formula VI

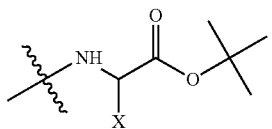

wherein X is hydrogen or C₁₋₄ alkyl;
with the proviso that the peptidomimetic includes at least one of Formula I, Formula II, Formula III, Formula IV, Formula V or Formula VI; and (b) a CFTR corrector, CFTR potentiator, mucolytic, anti-inflammatory agent or a combination thereof.

6. The kit of claim 5, wherein the peptidomimetic further comprises a label, one or more post-translational modifications, and/or a cell-penetrating sequence.

7. A method for treating cystic fibrosis comprising administering to a subject in need of treatment an effective amount of a peptidomimetic comprising the sequence NH₂-Xaa₁-Xaa₂-Xaa₃-Xaa₄-Xaa₅-Xaa₆ (SEQ ID NO:4), wherein:

(i) Xaa₁ is Met, Phe, Leu, Ala, Trp, diaminobutyric acid, diaminopropionic acid or a residue of Formula I, Formula I

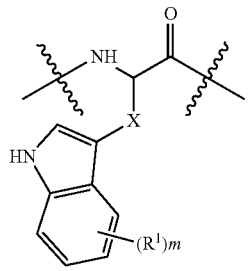

wherein X is —CH₂— or —(CH₂)ₙ—NH—, m is 1 to 4, n is 1 to 4, and each occurrence of R¹ is a tert-butyl group;

(ii) Xaa₂ is Gln, Pro, Phe, S-pipecolic acid or a residue of Formula II,

Formula II

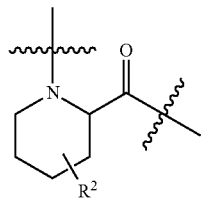

wherein R² is substituted at least one time anywhere on the ring and is a hydrogen, hydroxyl, methyl, amino, cyano, halo, nitro, mercapto, or phosphate group;

(iii) Xaa$_3$ is Ser, Val, Thr or a residue of Formula III,

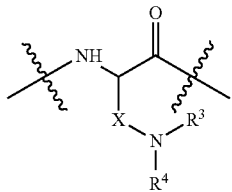

Formula III wherein X is —(CH$_2$)$_n$—, n is 1 to 4, and R$^3$ and R$^4$ are independently a hydrogen or methyl group;

(iv) Xaa$_4$ is Ser, Thr or a residue of Formula IV,

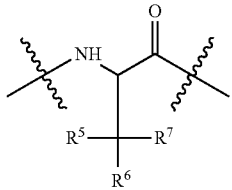

Formula IV wherein R$^5$, R$^6$ and R$^7$ are each independently a hydrogen, hydroxyl, methyl, amino, cyano, halo, nitro, mercapto, or phosphate group, with the proviso that at least one of R$^5$, R$^6$ or R$^7$ is a hydroxyl group;

(v) Xaa$_5$ is Lys, Arg, Ile or a residue of Formula V,

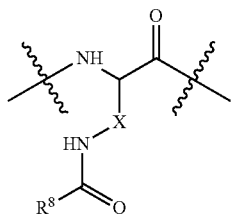

Formula V wherein X is —(CH$_2$)$_n$—, n is 1 to 4, and R$^8$ is a substituted aryl, heteroaryl, cycloalkyl or heterocycloalkyl; and (vi) Xaa$_6$ is Ile, Val, tert-butyl glycine and tert-butyl alanine or a residue of Formula VI,

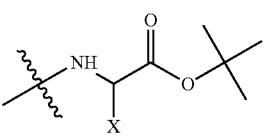

Formula VI wherein X is hydrogen or C$_{1-4}$ alkyl;
with the proviso that the peptidomimetic includes at least one of Formula I, Formula II, Formula III, Formula IV, Formula V or Formula VI, thereby treating the subject's cystic fibrosis.

8. The method of claim 7, further comprising administering a CFTR corrector, CFTR potentiator, mucolytic, anti-inflammatory agent or a combination thereof.

* * * * *